United States Patent
Hennige et al.

[11] Patent Number: 5,520,188
[45] Date of Patent: May 28, 1996

[54] ANNULAR ARRAY TRANSDUCER

[75] Inventors: Carl W. Hennige, San Jose; Stan DeMarta, Pleasanton; Claudio I. Zanelli, Sunnyvale, all of Calif.

[73] Assignee: Focus Surgery Inc., Fremont, Calif.

[21] Appl. No.: 333,471

[22] Filed: Nov. 2, 1994

[51] Int. Cl.⁶ .......................................................... A61B 8/00
[52] U.S. Cl. ........................................ 128/662.03; 310/367
[58] Field of Search ......................... 128/660.06, 660.07, 128/660.03, 660.08, 660.09, 661.01, 662.03; 73/625, 626; 310/334, 365, 366, 367, 369

[56] References Cited

U.S. PATENT DOCUMENTS 4,757,820  7/1988  Itoh ...................................... 128/660.03
4,865,042  9/1989  Umemura et al. .................. 128/660.03

*Primary Examiner*—George Manuel
*Attorney, Agent, or Firm*—Blakely, Sokoloff, Taylor & Zafman

[57] ABSTRACT

A transducer for use in a localization and therapeutic ultrasound system. The transducer of the present invention includes multiple elements that are driven separately. The elements operate together to focus a continuous wave ultrasound beam at a focal zone that is at a variable distance from the elements. The transducer includes a mechanism to adjust the focal distance so that the focal zone may be moved to multiple depths.

18 Claims, 4 Drawing Sheets

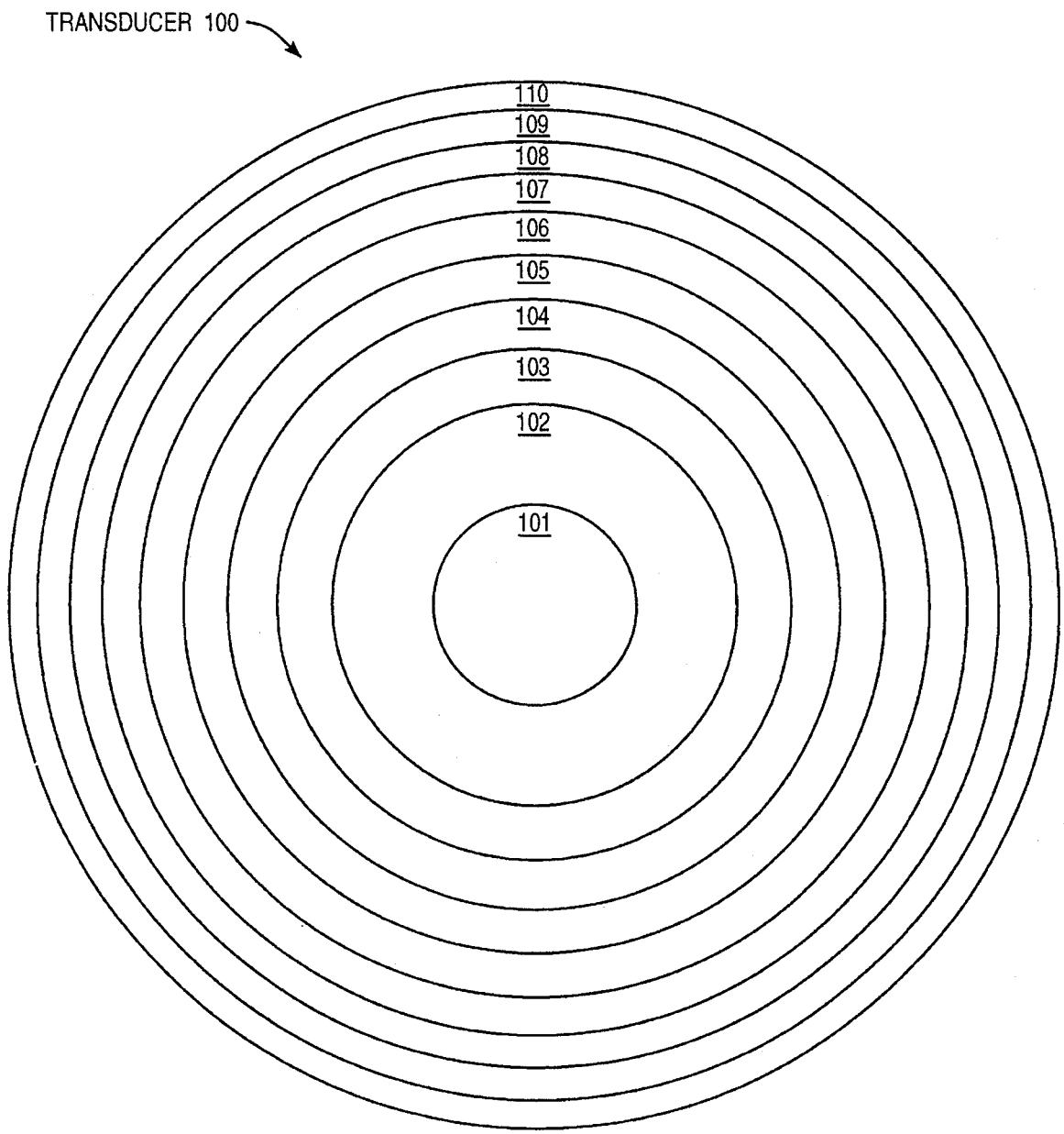
FIG_1

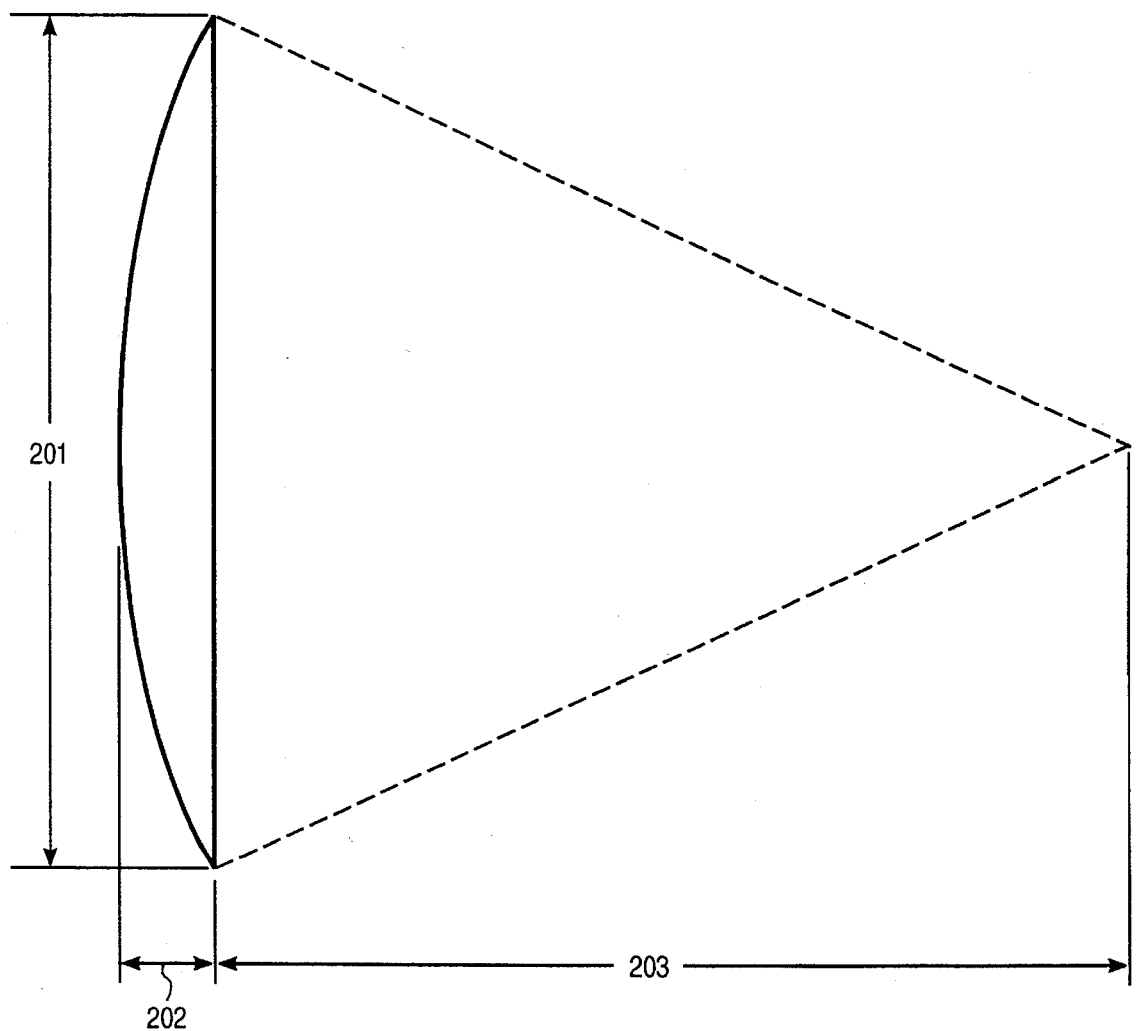
FIG_2

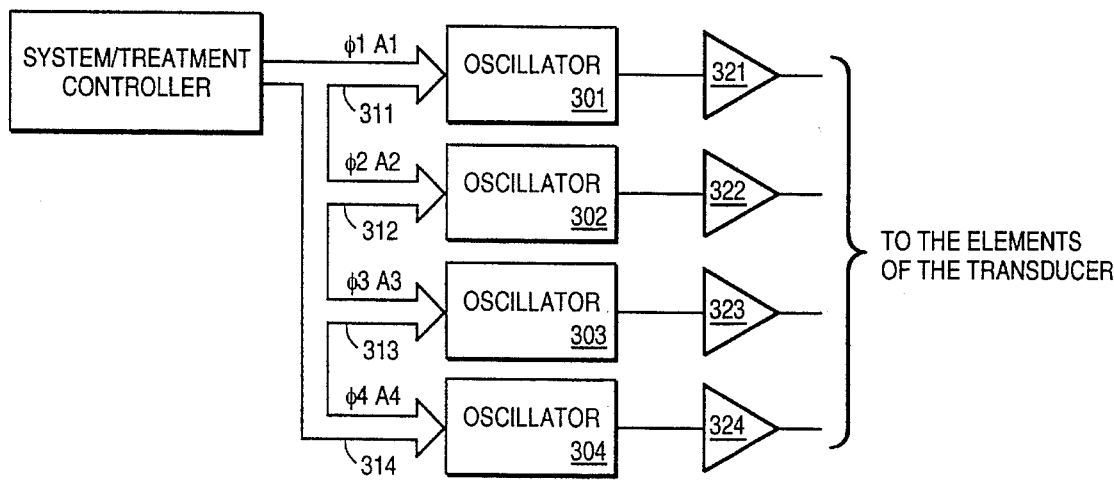
FIG_3
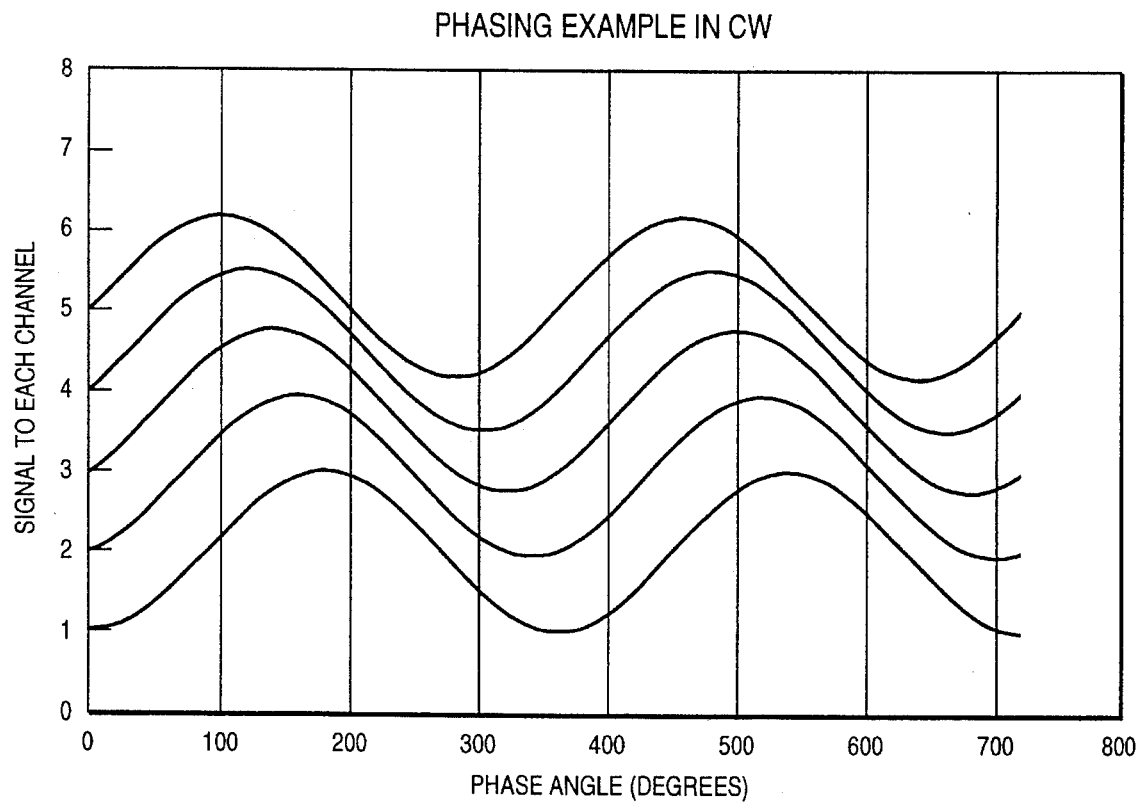
FIG_4

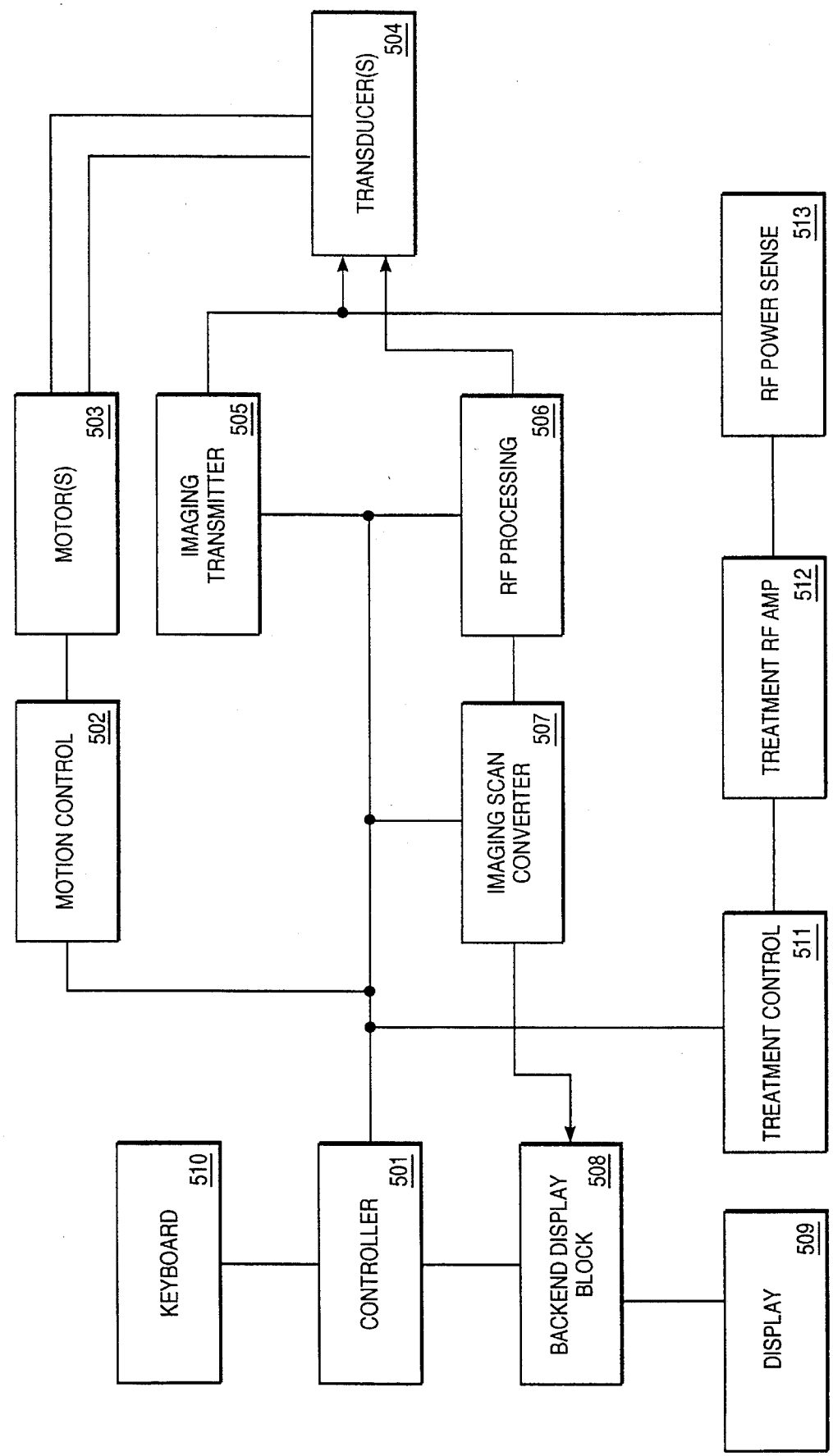
FIG_5

ANNULAR ARRAY TRANSDUCER

FIELD OF THE INVENTION

The present invention relates to the treatment of disease, tumors, etc., by the use of ultrasonic waves; more particularly, the present invention relates to transducers that provide treatment by focusing ultrasonic waves at a desired location in the body.

BACKGROUND OF THE INVENTION

Many diseases manifest themselves in a localized manner. These diseases include, for example, diseases of the breast, liver and prostate. Surgical procedures have traditionally been employed after medicinal approaches have been shown to be unsuitable or ineffective. Surgery, however, may still subject a patient to a significant risk and may not be completely effective.

Some non-invasive techniques have been utilized in the prior art for treating diseases of tissues, organs and the like. For instance, one known non-invasive treatment is high-intensity focused ultrasound (HIFU) to produce volume lesions at the site of the diseased tissue within the body. In HIFU, the acoustic energy applied to treat a location in the body results in the therapy.

The ultrasound systems of the prior art usually employ a transducer to apply the ultrasound waves (e.g., the therapy). The transducer is often larger, and radiates higher power, than those used for imaging and visualization in the prior art. Illustrative systems are described in U.S. Pat. Nos. 4,484,569 and 4,858,613. In some systems, a single transducer is used for visualization and therapy. For instance, in U.S. Pat. No. 5,117,832, entitled "Curved Rectangular/Elliptical Transducer", by Sanghvi et al., an ultrasound transducer is described that includes element(s) that provide imaging and elements that provide therapy.

As a general rule, the maximum total acoustic power (TAP) output from an ultrasound transducer is a function of the area of the radiating surface of the transducer. To generate the high power necessary for certain therapies, large radiating surfaces are needed. One problem associated with non-invasive therapies such as HIFU is that the high intensity ultrasonic waves used are capable of damaging the surface of the body where the waves enter it. For example, this may cause undesired damage to the skin. It is desirable to use a high acoustic power for therapy in such a way as to reduce the damaging affects on the body at the entrance location of the ultrasonic waves.

In order to treat a volume of tissue within the body, the focal zone must be moved along all three dimensions. This is accomplished in prior art by moving the transducer, both along a plane parallel to the surface of the body, as well as towards and away from the body. However, due to limitations of space around the area to be treated, in some cases the transducer cannot be moved closer to the body to achieve therapy into a deeper location. Also, moving the transducer away from the body in order to treat regions closer to the surface may not be practical because the ratio of dosage at the focal zone relative to the entrance surface diminishes, which may result in damage to the tissue at the surface. A common approach in the prior art is to use one transducer of a shorter focal distance to treat volumes closer to the surface, and another transducer of a longer focal distance to treat volumes farther from the surface. But changing transducers is time consuming and, in some cases, uncomfortable to the patient.

For these reasons it is desirable to change the depth of the focal zone of a transducer without moving the transducer towards or away from the body.

The present invention provides a transducer for use in a treatment system. The transducer of the present invention is able to vary the depth of focus. The present invention is able to vary the location of the focus without varying the acoustic energy received at the different depths. The present invention is able to vary the focus while maintaining a high ratio between the intensity at the focal zone in relation to the intensity at the entrance surface.

SUMMARY OF THE INVENTION

A transducer for use in a localization and therapeutic ultrasound system is described. The transducer of the present invention includes multiple elements that are individually driven. The elements operate together to focus a continuous wave ultrasound beam. The transducer includes a mechanism to adjust the focal distance so that the focal zone may be moved to multiple depths within the body.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 1 illustrates a front view of a circular section radiating surface transducer.

FIG. 2 illustrates a side view of the transducer depicted in FIG. 1.

FIG. 3 is a diagram of the electronics for driving the elements of the transducer of the present invention.

FIG. 4 is an example illustrating the combining of continuous wave driving signals of different phases, applied to multiple elements of the transducer to change the focal point of the acoustic beam.

FIG. 5 is a block diagram of one embodiment of the system of the present invention.

DETAILED DESCRIPTION OF THE PRESENT INVENTION

A transducer for use in an ultrasound system is described. In the following detailed description of the present invention, numerous specific details are set forth, such as specific number of rings, diameters and radii, frequencies, on/off times, etc., in order to provide a thorough understanding of the present invention. However, it will be understood to one skilled in the art that the present invention may be practiced without these specific details. In other instances, well-known structures and devices are shown in block diagram form, rather than in detail, in order to avoid obscuring the present invention.

FIG. 1 illustrates one embodiment of the transducer of the present invention. The transducer of the present invention is capable of producing high intensity focused ultrasound (HIFU). The transducer of the present invention generates a high power ultrasonic beam capable of ablating tissue at varying depths. Although the transducer of the present invention is capable of ablating tissue at varying depths, the transducer also maintains a high ratio between the intensity at the focal zone relative to the intensity at the entrance surface (e.g., 50 to 1, 60 to 1, 200 to 1, etc.).

Referring to FIG. 1, transducer 100 is shown having multiple elements. In one embodiment, transducer 100 comprises multiple concentric circular annuli, or ring-shaped transducer elements, forming an annular array. In the embodiment shown, transducer 100 includes ten circular annuli (elements 101–110). Although ten annuli are shown, the transducer of the present invention may include any number of annuli, such as two or more annuli.

Each element in transducer 100 has a width extending from the outer edge of the adjacent inner element to the inner edge of the adjacent outer element, with the exception of the inner most and outer most elements. As for the outer most element, its width is selected based on a design choice in view of the transducer's application and the size constraints on the overall diameter of the transducer array.

FIG. 2 illustrates a side view of the annular array transducer 100 shown in FIG. 1, having a height 201 and a depth 202. Also in FIG. 2, transducer 100 has a natural focal distance 203 (i.e., spherical bowl radius of curvature).

The transducer of the present invention is constructed with spherically curved piezoelectric elements. The assembly techniques of such a transducer are well-known to those skilled in the art.

One embodiment of the transducer of the present invention has elements with radii such as those listed in Table 1. Referring to Table 1, the radius listed for each of the elements is the distance to the outer edge of the circular annuli.

TABLE 1

| Element No. | Radius (mm) |
| --- | --- |
| 101 | 9.5 |
| 102 | 19.3 |
| 103 | 25.5 |
| 104 | 30.5 |
| 105 | 34.6 |
| 106 | 38.3 |
| 107 | 41.7 |
| 108 | 44.7 |
| 109 | 47.5 |
| 110 | 50.0 |

The height and diameter of the transducer is 10 cm, with a transducer width of 13 mm. This transducer has a focal distance that may be adjusted between 81 mm and 130 mm (for an operating frequency of 1.25 MHz).

In the present invention, transducer 100 of the present invention transmits a continuous wave (CW) ultrasound beam. Transducer 100 generates CW ultrasonic signals in response to signals from well-known driving electronics coupled to each of elements 101–110. These electronics are integrated into the system described later in conjunction with FIG. 5. In the present invention, each of the elements 101–110 is driven by a dedicated amplifier. Specifically, an oscillator generates the CW signal that is amplified and used to drive one of the elements 101–110.

The CW ultrasonic signals from each of elements 101–110 undergo constructive interference at the focal point.

The size of the elements 101–110 in transducer 100 is chosen to facilitate changing the location of the focal point of the transducer of the present invention. In the present invention, the radii of the elements are selected to maintain a specific phase separation. In one embodiment, the radii of the elements are selected to maintain a λ/4 phase separation. The position of the focal zone may be selected by adjusting the phase of the signals imparted to each element. In one embodiment, the phase is adjusted in the range of ±π/4. Therefore, by adjusting the phase of the signals that drive each element of the transducer, the present invention is able to change the depth of focus.

In one embodiment, the phases are changed using a series of independent oscillators, each having its own amplifier. An example of such a configuration is shown in FIG. 3. Referring to FIG. 3, oscillators 301–304 are coupled to receive input signals 311–314 respectively. The outputs of oscillators 301–304 are coupled to drive amplifiers 321–324 respectively. Each of the drive amplifiers 321–324 drives one of the elements of the transducer of the present invention. Although only four oscillators and four drive amplifiers are shown in FIG. 3, a separate and distinct oscillator and drive amplifier may be coupled to each element in the transducer array in the present invention. Note that in one emodiment, most elements have a separate and distinct oscillator and drive amplifier, while a small number of elements are driven with a common oscillator and drive amplifier.

Oscillators 321–324 are loaded via digital electronics with phase and magnitude information. In one embodiment, the phase (∅) and magnitude (A) information are loaded by a controller in the system (e.g., a treatment, or therapy, controller). In response to the inputs, each of oscillators 301–304, being simple sinusoid generators in one embodiment, drive amplifiers 321–324, which in turn provide electrical signals to the elements of the annular array transducer of the present invention. Each of the elements then generates CW ultrasound waves, such that the waves interfere constructively with each other at a location that is varied by the corresponding phases, thereby focusing the beam at a specific distance from the transducer.

In order to change the focus, the phase information provided to oscillators 301–304 is changed. The change in phase causes the continuous wave ultrasound signals to interfere with one another in such as way as to create a focus nearer or farther than its previous position.

It should be noted that the phase information received by the oscillators may be changed dynamically during therapy (in real-time). In this manner, the focal depth can be changed in real-time. For instance, a specific volume could be identified for treatment and then the controller can provide the necessary phase and amplitude information to cause the focal depth to change in order for the volume to receive treatment.

An example of the CW ultrasound wave driving signals of different phases, applied to multiple elements of the transducer to change the focal point of the acoustic beam is shown in FIG. 4.

In using the transducer of the present invention for therapy, because focus may be shifted in real-time, the beam may be swept through a portion of tissue in order to create a lesion of a specific size.

The transducer of the present invention may be used to provide imaging capabilities in conjunction with its therapy capabilities. For instance, one or more of the elements of the transducer may be used to provide ultrasound imaging. In one embodiment, imaging is performed by the central element (101). In another embodiment, the central element (101) may be replaced by an element specifically designed for imaging. When the transducer is being used for imaging, the central element can be activated alone. This produces the conventional image which the diagnostician regularly views and interprets. Then, when treatment is being conducted, the amplifiers responsible for driving the elements of the transducer are energized.

FIG. 5 is a block diagram of one embodiment of the localization and therapy system that may use the transducer of the present invention. By using computer control and moving the region of high intensity though a predetermined three-dimensional region, many small lesions are created, thereby resulting in a volummetric destruction of tissue.

Referring to FIG. 5, the system includes controller 501, motion control 502, motor(s) 503, transducers 504, imaging transmitter 505, radio frequency (RF) processing 506, imaging scan converter 507, display block 508, display 509, keyboard 510, phase control 511, RF amplifiers 512, and RF power sense block 513. Controller 501 is coupled to motion control 502, imaging transmitter 505, radio frequency (RF) processing 506, imaging scan converter 507, display block 508, and keyboard 510 in order to control the operation of the system. Specifically, controller 501 controls the therapy provided by the system. Motor(s) 503 are coupled to motion control 502 and transducer(s) 504 to control their movement in response to control signals provided to motor(s) 503 from motion control 502 (and controller 501). Transducers 504 are also coupled to imaging transmitter 505, RF processing 506 and RF power sense block 513. RF processing 506 is coupled to imaging scan converter 507. Imaging scan converter 507 is coupled to display block 508. Display 509 is coupled to display block 508. RF power sense block 513 is also coupled to treatment RF amp 512. RF amplifier 512 is coupled to treatment control 511. In one embodiment, controller 501 includes a computer having a processor, bus, memory, as well as input/output devices.

Imaging transmitter 505, RF processing 506, scan converter 507, display block 508 and display 509, in conjunction with the transducer(s) 504 and under the control of controller 501, function together as an ultrasound imaging system. The ultrasound imaging system allows the user of the system to visualize a treatment area in the body to receive treatment, as well as obtain data corresponding to the size, shape and location of diseased tissue and/or tumors in the body. The imaging system may include real-time ultrasound B-mode imaging capabilities. It should be noted that other types of imaging systems, such as MRI or CRT imaging systems or other sonographic imaging systems, may be used as an alternative.

Under the direction of controller 501, imaging transmitter 505 causes an imaging transducer included with transducer(s) 504 to transmit ultrasonic pulses into the body. Echoes are reflected back to the imaging transducer and represent information about the body. The imaging transducer converts the ultrasonic echoes into electrical signals which are received by RF processing block 506. The signal may undergo filtering and then undergo further signal processing, such as demodulation, additional filtering, and other processing well-known to those skilled in the art. The processed electronic signal is then sent to scan converter 507 for spatial registration as part of an ultrasound image. That is, scan converter 507 stores vector information from a single line of the ultrasound image and converts such vector information into a format suitable for display, such as raster scan, on display 509. The converted information is sent to display block 508 which contains image memory for display 109. The display block 508 may also include post-processing tools to allow image processing of the data prior to or subsequent to being displayed. In one embodiment, display 509 may comprise a standard television or computer type monitor. In one embodiment, display 509 may comprise multiple displays. The operation of the ultrasound imaging system of the present invention is well-known by those skilled in the art and its operation will not be discussed further.

Using the imaging portion of the system, images of portions of the body may be displayed on display 509 to identify the treatment area. Using a trackball located on keyboard 510, an appropriate zone of ablation is delineated and stored in memory (not shown) in the system under the control of controller 501. The trackball may be separate from keyboard 510 in some embodiments. Thus, from the visualization of the body, the treatment volume is defined. Also by interacting with the tissue and organs displayed on display 509, the treatment spatial regimen is computed. Dosage parameters of sound intensity and time-on period are entered into the system.

Once a treatment area and regimen have been defined, transducer(s) 504 are positioned to provide therapy to the treatment area. In one embodiment, transducer(s) 504 are positioned using motor(s) 503 via control from motion control 502 in order to direct and focus an ultrasound beam to the treatment area. In other embodiments, transducer(s) 504 may be electrically manipulated in order to direct ultrasound waves as therapy to the treatment area.

Thus, the present invention provides an annular array transducer having multiple elements, each of which is activated by separate electronics, to provide a continuous wave ultrasound beam for therapy. The transducer of the present invention is capable of changing its depth of focus by changing the phase of the signals driving the elements.

By changing the depth of focus, the present invention provides a treatment system that is able to vary the location of the lesions. This allows a single treatment device, or transducer, to supply therapy to locations at multiple focal depths within the body. Moreover, the therapy system of the present invention is able to vary the acoustic energy delivered to the focal region.

Whereas many alterations and modifications of the present invention will no doubt become apparent to a person of ordinary skill in the art after having read the foregoing description, it is to be understood that the particular embodiment shown and described by way of illustration is in no way intended to be considered limiting. Therefore, references to details of the preferred embodiment are not intended to limit the scope of the claims which in themselves recite only those features regarded as essential to the invention.

Thus, an annular array transducer has been described.

We claim:

1. An ultrasound transducer for use in a visualization and therapy system comprising:

a first curved element operable in a plurality of modes, wherein the first curved element provides for imaging in one of the plurality of modes and provides therapy in a second of the plurality of modes;

a second curved element coupled to the first curved element and operable in the second of the plurality of modes, wherein the first curved element and the second curved element operate in combination to provide therapy when in the second of the plurality of modes.

2. The transducer defined in claim 1 wherein the second curved element surrounds the first curved element, such that the first curved element is a central element of the transducer.

3. The transducer defined in claim 1 wherein the second curved element is off in said one of the plurality of modes.

4. A transducer assembly comprising:

a plurality of curved elements, wherein each of the plurality of curved elements is driven separately by one of a plurality of signals to generate energy waves as a continuous wave focused at a focal zone a focal distance from the plurality of curved elements, such that an acoustic beam is created by the plurality of curved elements; and means coupled to the plurality of curved elements for adjusting the focal distance to move the focal zone to one of a plurality of depths while maintaining a same amount of acoustic energy at different depths.

5. The transducer assembly defined in claim 4 wherein each of the plurality of curved elements comprises a concentric circular element, such that the plurality of curved elements form an annular array.

6. The transducer assembly defined in claim 4 wherein each of the plurality of curved elements have substantially the same surface area.

7. The transducer assembly defined in claim 6 wherein each of the plurality of curved elements has a radius selected to maintain a fixed phase separation.

8. The transducer assembly defined in claim 7 wherein the phase separation comprises a $\pi/4$ phase separation.

9. The transducer assembly defined in claim 6 wherein one of the plurality of curved elements is centrally located among the plurality of concentric circular annuli, and further wherein said one of the plurality of curved elements is designed for imaging.

10. The transducer assembly defined in claim 4 wherein the focal distance is adjusted by adjusting the phase of the plurality of signals imparted to each of the plurality of curved elements.

11. The transducer assembly defined in claim 10 wherein the means for adjusting includes means for varying the phase of each of the plurality of signals in the range of $\pm\pi/4$.

12. The transducer assembly defined in claim 4 wherein the means for adjusting comprises drive electronics.

13. A transducer assembly comprising:

a plurality of concentric circular curved annuli coupled as an annular array, wherein each of the plurality of concentric circular curved annuli is driven separately by one of a plurality of signals to generate ultrasound waves as a continuous wave focused at a focal point a focal distance from the plurality of concentric circular curved annuli; and a drive mechanism coupled to the plurality of concentric circular curved annuli, wherein the drive mechanism adjusts the focal distance to one of a plurality of depths by adjusting the phase of the plurality of signals while maintaining a same amount of acoustic energy at different depths.

14. The transducer assembly defined in claim 13 wherein each of the plurality of concentric circular annuli have substantially the same surface area.

15. The transducer assembly defined in claim 13 wherein each of the plurality of concentric curved circular annuli has a radii selected to maintain a fixed phase separation.

16. The transducer assembly defined in claim 15 wherein the phase separation comprises a $\pi/4$ phase separation.

17. The transducer assembly defined in claim 13 wherein one of the plurality of concentric circular curved annuli is centrally located and is designed for imaging.

18. The transducer assembly defined in claim 13 wherein the drive mechanism varies the phase of each of the plurality of signals in the range of $\pm\pi/4$.

* * * * *